(12) United States Patent
Zhou (10) Patent No.: US 11,576,763 B2
(45) Date of Patent: Feb. 14, 2023

(54) VISUAL TOOTH CLEANING, GRINDING AND POLISHING INSTRUMENT

(71) Applicant: Xing Zhou, Guangzhou (CN)

(72) Inventor: Xing Zhou, Guangzhou (CN)

( * ) Notice: Subject to any disclaimer, the term of this patent is extended or adjusted under 35 U.S.C. 154(b) by 33 days.

(21) Appl. No.: 16/832,319

(22) Filed: Mar. 27, 2020

(65) Prior Publication Data

US 2020/0222160 A1 Jul. 16, 2020

Related U.S. Application Data

(63) Continuation of application No. PCT/CN2018/100719, filed on Aug. 15, 2018.

(30) Foreign Application Priority Data

Oct. 13, 2017 (CN) .......................... 201710949495.6

(51) Int. Cl.
*A61C 15/04* (2006.01)
*A61B 1/247* (2006.01)
(Continued)

(52) U.S. Cl.
CPC .............. *A61C 15/048* (2013.01); *A61B 1/06* (2013.01); *A61B 1/247* (2013.01); *A61C 17/221* (2013.01); *A61C 17/3481* (2013.01)

(58) Field of Classification Search
CPC ... A61C 17/221; A61C 17/3481; A61C 17/36; A61C 17/22; A61C 17/0202;
(Continued)

(56) References Cited

U.S. PATENT DOCUMENTS 5,230,621 A 7/1993 Jacoby
5,286,192 A * 2/1994 Dixon ................ A61C 17/0202
601/162
(Continued)

FOREIGN PATENT DOCUMENTS

CN 102405027 A 4/2012
CN 104905547 A 9/2015
(Continued)

OTHER PUBLICATIONS

Zhou, Extended European Search Report, EP18866013.8, dated May 26, 2021, 10 pgs.
(Continued)

*Primary Examiner* — Heidi M Eide
(74) *Attorney, Agent, or Firm* — Morgan, Lewis & Bockius LLP (57) ABSTRACT

A visual tooth cleaning, grinding and polishing instrument includes a host, an oral observation instrument and a cleaning and polishing tool. The host can drive the cleaning and polishing tool and supply a power source and a control system for an illuminating system, an observation system and the oral observation instrument. A picture shot by a camera of the observation system can be transmitted to a display of the observation system in time, so as to achieve the purposes of cleaning the teeth while observing a process of cleaning the dental calculus, dental plaque and pigmentation on the surface of the teeth with the cleaning and polishing tool and the cleaning effect instantly on a mobile phone, thereby effectively cleaning, grinding and polishing the teeth. A flusher or an electric toothbrush head or other interdental cleaning tools may also be mounted on the host or the oral observation instrument.

17 Claims, 10 Drawing Sheets

(51) Int. Cl.
*A61C 17/22* (2006.01)
*A61B 1/06* (2006.01)
*A61C 17/34* (2006.01)

(58) Field of Classification Search
CPC ......... A61C 17/005; A61B 1/06; A61B 1/247; A61B 5/0088
See application file for complete search history.

(56) References Cited

U.S. PATENT DOCUMENTS

| | | | | |
|---|---|---|---|---|
| 5,613,259 | A * | 3/1997 | Craft | A61C 17/3481 15/22.1 |
| 6,247,477 | B1 * | 6/2001 | Wagner | A45D 44/18 132/309 |
| 2001/0012605 | A1 * | 8/2001 | Kawamura | A61C 17/0202 433/29 |
| 2003/0031979 | A1 * | 2/2003 | Shortt | A61C 17/40 433/125 |
| 2004/0079384 | A1 | 4/2004 | Lai et al. | |
| 2005/0004498 | A1 * | 1/2005 | Klupt | A61C 17/222 433/80 |
| 2009/0162810 | A1 * | 6/2009 | Werner | A61C 17/20 433/119 |
| 2012/0077145 | A1 * | 3/2012 | Tsurukawa | A46B 11/0089 433/80 |
| 2013/0061412 | A1 * | 3/2013 | Vashi | A61B 5/0088 15/106 |
| 2013/0171582 | A1 | 7/2013 | Nishikibe et al. | |
| 2014/0199651 | A1 * | 7/2014 | Adachi | A61C 17/20 433/27 |
| 2015/0257636 | A1 * | 9/2015 | Kohler | A61B 1/00087 433/29 |

FOREIGN PATENT DOCUMENTS

| | | |
|---|---|---|
| CN | 205947879 U | 2/2017 |
| JP | S63109807 A | 5/1988 |
| JP | 2001212161 A | 8/2001 |
| JP | 2003241104 A | 8/2003 |
| JP | 2004202065 A | 7/2004 |
| JP | 2007510454 A | 4/2007 |
| JP | 2009136486 A | 6/2009 |
| JP | 2015002921 A | 1/2015 |
| JP | 2017047146 A | 3/2017 |
| JP | 2017514639 A | 6/2017 |
| WO | WO2011077820 A1 | 6/2011 |

OTHER PUBLICATIONS

Zhou, International Search Report and Written Opinion, PCT/CN2018/100719, dated Nov. 9, 2018, 11 pgs.
Zhou, International Preliminary Report on Patentability, PCT/CN2018/100719, dated Apr. 14, 2020, 4 pgs.
Zhou, Office Action, JP2020-518724, Notice of Reasons for Refusal, dated Jun. 27, 2022, 17 pgs.

\* cited by examiner

VISUAL TOOTH CLEANING, GRINDING AND POLISHING INSTRUMENT

CROSS-REFERENCE TO RELATED APPLICATIONS

This application is a continuation application of PCT/CN2018/100719, entitled "DEVICE FOR VIEWABLE TEETH-CLEANING AND POLISHING" filed on Aug. 15, 2018, which claims priority to Chinese Patent Application No. 201710949495.6, entitled "DEVICE FOR VIEWABLE TEETH-CLEANING AND POLISHING" filed with the China National Intellectual Property Administration on Oct. 13, 2017, all of which are incorporated by reference in their entirety.

FIELD OF THE INVENTION

The invention relates to a tool for oral cleaning, and particularly relates to a visual tooth cleaning, grinding and polishing instrument for cleaning teeth, interdental spaces and oral cavities.

BACKGROUND OF THE INVENTION

When the teeth are not cleaned thoroughly for a long time or when people smoke, drink tea or drink alcohol for a long time, it is very easy to cause dental problems such as dental calculus, dental plaque and pigmentation on the surface of the teeth. At present, usually, the dental problems such as dental calculus, dental plaque and pigmentation are solved by washing the teeth in a professional stomatological hospital.

At present, the common way to clean the dental calculus, dental plaque and pigmentation in a process of washing the teeth is to extend a work head of a tooth cleaner in high-speed rotation or vibration into the oral cavity so as to loosen the dental plaque and break the dirt on the surface of the teeth under the friction or vibration action of the work head, thereby achieving the purpose of cleaning the dental calculus, dental plaque and pigmentation.

Because the work head needs to be extended into the oral cavity and the light in the oral cavity is very dark, it is very difficult to see the condition in the oral cavity. Therefore, in the prior art, generally, the dental calculus, dental plaque, pigmentation, coated tongue and the like in the oral cavity of a patient can only be cleaned by a dentist by virtue of professional instruments and a dental treatment table or a dental treatment chair in a dental clinic.

At home, it is difficult for a patient to use the oral cleaning instruments in the prior art to clean the dental calculus, dental plaque, pigmentation and the like in the oral cavity. Generally, the patient can only use a coated tongue cleaner, various toothbrushes or flusher to clean the teeth, dorsum and the like. Because the light in the oral cavity is dark or the parts to be cleaned are relatively hidden and are difficult to observe, the patient can only perform these cleaning operations by feeling, so that the parts to be cleaned always cannot be cleaned, but the parts that do not need to be cleaned are cleaned repeatedly, causing excessive damage to the teeth. In particular, when the patient uses a tool in high-speed rotation or vibration, such as a high speed grinding head, an ultrasonic grinding head or a dental bur, to clean the oral cavity by himself, once the work head deviates from the work part, it is very easy to cause accidental injury.

In order to overcome the defects of the prior art, it is necessary to develop a tool which can be used by the patient at home to carry out targeted cleaning, grinding and polishing on the teeth or coated tongue by using a display screen of a mobile phone in a visual state.

SUMMARY

A visual tooth cleaning, grinding and polishing instrument of the invention is capable of cleaning, grinding and polishing the teeth in a visual state by utilizing a special cleaning and polishing tool, thereby effectively solving the oral problems of dental calculus, dental plaque, pigmentation and the like.

The visual tooth cleaning, grinding and polishing instrument 900 is characterized by including a host 100, an oral observation instrument 200 and a cleaning and polishing tool 400;

A. the host 100 includes a power system 11, a circuit system 12, a control system 13, a moving system 14 and a housing 15; the power system 11, the control system 13 and the moving system 14 are connected together through the circuit system 12; the cleaning and polishing tool 400 is connected to the moving system 14 and is mounted on the host 100;

B. the oral observation instrument 200 includes a housing 21, an illuminating system 23, an observation system 24 and a switch 26; the illuminating system 23, the observation system 24, the power system 11 and the switch 26 are connected together through the circuit system 12 and the control system 13; the oral observation instrument 200 is connected to the host 100;

C. the work part of the cleaning and polishing tool 400 is within the field of view of the observation system 24 of the oral observation instrument 200.

In the invention, the observation system 24 may be a camera system 24-1. The camera system 24-1 includes a camera 24-1-1, a data processing and output system 24-1-2 and a display 24-1-3. A picture shot by the camera 24-1-1 can be transmitted to the display 24-1-3 in time through the data processing and output system 24-1-2. The display 24-1-3 may be a smart phone 24-1-31, or a computer 24-1-32, or a liquid crystal display/television 24-1-33, or a tablet computer 24-1-34.

According to the visual tooth cleaning, grinding and polishing instrument of the invention, the oral observation instrument and the cleaning and polishing tool are effectively integrated together, and the circuit system 12 and the control system 13 can not only switch on the power system 11 to power the moving system 14 to enable the moving system 14 to drive the cleaning and polishing tool 400 to work, but also switch on the illuminating system 23, the observation system 24 and the switch 26 of the oral observation instrument 200 to supply power required for the work of the oral observation instrument 200 and control the oral observation instrument 200 to work. Therefore, in the present application, the host 100 can not only drive the cleaning and polishing tool 400 but also supply a power source and a control system for the illuminating system 23, the observation system 24 and the like of the oral observation instrument 200, and can transmit the picture shot by the camera 24-1-1 of the observation system 24 to the display 24-1-3 such as the smart phone 24-1-31 of the observation system 24 in time, so as to achieve the purposes of cleaning the teeth while observing a process of cleaning the dental calculus, dental plaque and pigmentation on the surface of the teeth with the cleaning and polishing tool 400 and the cleaning effect instantly on a mobile phone, thereby effectively cleaning, grinding and polishing the teeth.

Further, the moving system 14 is a vibration system capable of generating vibration or a rotation system capable of generating rotation.

The vibration system includes a vibration generation device 14-1 and a vibration transmission device 14-2 capable of transmitting the vibration generated by the vibration generation device 14-1, one end of the vibration transmission device 14-2 is connected to the vibration generation device 14-1, and the other end of the vibration transmission device 14-2 is connected to the cleaning and polishing tool 400.

The vibration generation device 14-1 is an electromagnetic vibration device including an electromagnetic vibrator, or a magnetic suspension motor, or a piezoelectric transducer.

The cleaning and polishing tool 400 is detachably mounted on the vibration transmission device 14-2. Generally, the cleaning and polishing tool 400 is detachably mounted at a distal end of the vibration transmission device 14-2. By virtue of a detachable mounting mode, the cleaning and polishing tool 400 can be conveniently removed from the host 100 for replacement, storage and carrying.

The cleaning and polishing tool 400 is detachably mounted on the vibration transmission device 14-2 in a mode of concave-convex clamping connection, or interference fit connection, or rotational connection. Herein, the applicant only enumerates the above three detachable connection modes, and those skilled in the art may design different connection modes according to actual requirements in combination with the prior art without departing from the scope of protection of the present application.

The illuminating system 23 and the observation system 24 are disposed at a front end 200-1 of the oral observation instrument 200, and the illuminating system 23 and the observation system 24 are connected to the host 100 through the circuit system 12 and the control system 13. After the power system 11 is switched on, the switch 26 is turned on, and then the host 100 can supply power for the oral observation instrument 200 through the circuit system 12 and the control system 13, and drive the illuminating system 23 and the observation system 24 of the oral observation instrument 200 to work.

The front end 200-1 of the oral observation instrument 200 is detachably mounted on the host 100. Because the front end 200-1 of the oral observation instrument 200 is detachably mounted on the host 100, after use, the oral observation instrument 200, the cleaning and polishing tool 400 and the cleaning and polishing tool 400 can be removed from the host so as to facilitate separate storage and cleaning.

The front end 200-1 of the oral observation instrument 200 is detachably mounted on the host 100 in a mode of rotational connection or concave-convex clamping connection. Herein, the applicant only enumerates the above two detachable connection modes, and those skilled in the art may design different connection modes according to actual requirements in combination with the prior art without departing from the scope of protection of the present application.

The front end 200-1 of the oral observation instrument 200 is foldably mounted on the host 100. After use, the oral observation instrument 200 can be folded and then stored so as to further facilitate carrying.

The front end 200-1 of the oral observation instrument 200 is foldably mounted on the host 100 through a rotating shaft type moving mechanism or a concave-convex clamping mechanism. Herein, the applicant only enumerates the above two detachable connection modes, and those skilled in the art may design different connection modes according to actual requirements in combination with the prior art without departing from the scope of protection of the present application.

The cleaning and polishing tool 400 includes a polishing work part 400-1 having grinding and polishing functions and geometrically shaped as a conical cleaning and polishing head 401, or a spherical cleaning and polishing head 402, or a flat cleaning and polishing head 403. Herein, the applicant only enumerates the polishing heads of the above several shapes, and those skilled in the art may design polishing heads of various shapes according to actual conditions in combination with the prior art without departing from the scope of protection of the present application.

The polishing work part 400-1 is provided with a flexible containing cavity 400-2 capable of containing polishing glue or toothpaste. A cleaning agent or a polishing agent such as polishing glue or polishing paste or toothpaste can be conveniently stored in the flexible containing cavity 400-2. In use, the polishing glue or polishing paste or toothpaste can be filled in the flexible containing cavity 400-2. When the polishing work part 400-1 works, the polishing glue or polishing paste or toothpaste in the flexible containing cavity 400-2 is compressed so as to further improve the cleaning effect of the polishing work part 400-1.

An electric toothbrush head 406 may also be mounted on the host 100 of the visual tooth cleaning, grinding and polishing instrument 900, and the electric toothbrush head 406 is connected to the moving system 14 of the host 100. When large-area cleaning of the teeth is required with an electric toothbrush, the cleaning and polishing tool 400 can be removed from the host 100 and replaced with the electric toothbrush head 406, and then, the circuit system 12 and the control system 13 can switch on the power system 11 to power the moving system 14 to enable the moving system 14 to drive the electric toothbrush head 406 to work to clean the oral cavity.

A work part 406-1 of the electric toothbrush head 406 is within the field of view of the observation system 24 of the oral observation instrument 200.

An interdental cleaning tool 400-9 may also be mounted on the host 100 or the oral observation instrument 200 of the visual tooth cleaning, grinding and polishing instrument 900, and the interdental cleaning tool 400-9 includes an interdental brush 407, or a dental floss 408, or a flusher 409, or a pair of fetching forceps 410, or a hair brush 411. The interdental cleaning tool 400-9 can effectively clean the interdental space or work in conjunction with the cleaning and polishing tool 400 to facilitate a cleaning process. For example, when the flusher 409 is mounted on the oral observation instrument 200, in a process of grinding the teeth by using the cleaning and polishing tool 400, the flusher 409 is used to spray water to flush the work part to rush away the ground dental calculus, dental plaque, dirt and the like from the surface of the teeth, so that the tooth grinding process is more comfortable and convenient.

A brush head 407-1 of the interdental brush 407, a line 408-1 of the dental floss 408, a water column sprayed by the flusher 409, a forceps head 410-1 of the fetching forceps 410 and a head 411-1 of the hair brush 411 are within the field of view of the observation system 24 of the oral observation instrument 200.

The interdental cleaning tool 400-9 is detachably mounted on the oral observation instrument 200 through a connecting mechanism 300. By virtue of a detachable connection mode, different interdental cleaning tools 400-9 can be replaced according to needs. When the interdental space needs to be transversely cleaned, the interdental brush 407 can be selectively mounted. When the interdental space needs to be longitudinally cleaned, the dental floss 408 can be selectively mounted. When there are foreign matters that need to be taken out, the fetching forceps 410 or the hair brush 411 can be selectively mounted.

The connecting mechanism 300 is a rotational connecting mechanism, or a concave-convex clamping connecting mechanism, or an interference fit connecting mechanism. Herein, the applicant only enumerates the above three detachable connection modes, and those skilled in the art may design different connection modes according to actual requirements in combination with the prior art without departing from the scope of protection of the present application.

The flusher 409 includes a sprayer 409-1, a water tank 409-2, a water pipe 409-3, a water spraying switch 409-4 and a pressurizing device 409-5, the water tank 409-2 and the pressurizing device 409-5 are mounted on a housing 15 of the host 100, and the sprayer 409-1 is mounted near the observation system 24 at the front end 200-1 of the oral observation instrument 200.

The pressurizing device 409-5 is an electric pressurizing device 409-51.

The electric pressurizing device 409-51 is an electric air pressurizing device or electric water pressurizing device 409-51-2.

The electric water pressurizing device 409-51-2 is a submersible pump 409-51-21 or a water pump.

The sprayer 409-1 of the flusher 409 may be built in the housing 21 of the front end 200-1 of the oral observation instrument 200.

The flusher 409 can be used in conjunction with the interdental brush 407, or the dental floss 408, or the fetching forceps 410, or the hair brush 411.

A direction of the water column sprayed by the flusher 409 is substantially the same as a direction in which the interdental brush 407 or the dental floss 408 enters the interdental space. When the flusher 409 is used in conjunction with the interdental brush 407 or the dental floss 408, the water column sprayed by the flusher 409, in the direction substantially the same as the direction in which the interdental brush 407 or the dental floss 408 enters the interdental space, is more favorable for cleaning the interdental space by the interdental brush 407 or the dental floss 408.

The visual tooth cleaning, grinding and polishing instrument of the invention includes a host 100, an oral observation instrument 200 and a cleaning and polishing tool 400. The host 100 can not only drive the cleaning and polishing tool 400 but also supply a power source and a control system for the illuminating system 23, the observation system 24 and the like of the oral observation instrument 200, and the picture shot by the camera 24-1-1 of the observation system 24 can be transmitted to the display 24-1-3 such as the smart phone 24-1-31 of the observation system 24 in time, so as to achieve the purposes of cleaning the teeth while observing a process of cleaning the dental calculus, dental plaque and pigmentation on the surface of the teeth with the cleaning and polishing tool 400 and the cleaning effect instantly on a mobile phone, thereby effectively cleaning, grinding and polishing the teeth. The electric toothbrush head 406 or the interdental cleaning tool 400-9, such as the interdental brush 407, or the dental floss 408, or the flusher 409, or the fetching forceps 410, or the hair brush 411, may also be mounted on the host 100 or the oral observation instrument 200 of the visual tooth cleaning, grinding and polishing instrument 900, so that the visual tooth cleaning, grinding and polishing instrument of the invention has multiple oral cleaning functions and can solve various oral cleaning problems in all aspects. In particular, the cleaning efficiency can be improved by performing grinding, polishing and cleaning by using the cleaning and polishing tool 400 while flushing with water by using the flusher 409.

BRIEF DESCRIPTION OF THE DRAWINGS

FIG. 1-1 is a schematic perspective view of the visual tooth cleaning, grinding and polishing instrument of the invention after the polishing and cleaning tool is mounted.

FIG. 2-1 is a cross-sectional view along A-A of FIG. 2.

FIG. 3-1 is a schematic perspective view of a cleaning and polishing tool including a flat polishing head.

FIG. 3-2 is a schematic perspective view of a cleaning and polishing tool having a flexible containing cavity.

FIG. 4-1 is a schematic perspective view of the visual tooth cleaning, grinding and polishing instrument of the invention after the electric toothbrush head is mounted.

FIG. 5-1 is a schematic perspective view of the visual tooth cleaning, grinding and polishing instrument of the invention after the interdental brush is mounted.

FIG. 6-1 is a schematic perspective view of the visual tooth cleaning, grinding and polishing instrument of the invention after the dental floss is mounted.

FIG. 7-1 is a schematic perspective view of the visual tooth cleaning, grinding and polishing instrument of the invention after the pair of fetching forceps is mounted.

FIG. 8-1 is a schematic perspective view of the visual tooth cleaning, grinding and polishing instrument of the invention after the hair brush is mounted.

IN THE ABOVE DRAWINGS host 100, oral observation instrument 200, connecting mechanism 300, cleaning and polishing tool 400, visual tooth cleaning, grinding and polishing instrument 900 of the invention;

front end 200-1 of oral observation instrument, threaded connecting mechanism 201.

On Host:

power system 11, circuit system 12, control system 13, moving system 14, housing 15:

power switch 13-1, vibration drive switch 13-2;

vibration generation device 14-1, vibration transmission device 14-2, transmission shaft connecting part 14-2-1, connecting groove 14-2-11, rotation stopping convex step 14-2-12, connecting shaft 14-2-13;

electrical mounting space 15-1, water and water path mounting space 15-2.

On Oral Observation Instrument:

housing 21, illuminating system 23, observation system 24, switch 26;

camera system 24-1;

camera 24-1-1, data processing and output system 24-1-2, display 24-1-3;

smart phone 24-1-31, computer 24-1-32, liquid crystal display/television 24-1-33, tablet computer 24-1-34.

On Connecting Mechanism:

positioning block 31 for mounting oral irrigator on oral observation instrument, positioning groove 32 for mounting oral irrigator on oral observation instrument, clamping block 33 for mounting oral irrigator on oral observation instrument.

On Cleaning and Polishing Tool:

cleaning and polishing work part 400-1, flexible containing cavity 400-2, interdental cleaning tool 400-9;

conical cleaning and polishing head 401, spherical cleaning and polishing head 402, flat cleaning and polishing head 403, electric toothbrush head 406, interdental brush 407, dental floss 408, flusher 409, fetching forceps 410, hair brush 411;

brush head 407-1, line 408-1 of dental floss, forceps head 410-1, head 411-1 of hair brush;

sprayer 409-1, water tank 409-2, water pipe 409-3, water spraying switch 409-4, pressurizing device 409-5, water filling hole 409-6;

electric pressurizing device 409-51;

electric water pressurizing device 409-51-2, submersible pump 409-51-21, water inlet system 409-51-211, pressurizing system 409-51-212, drainage system 409-51-213;

connecting elastic sheet 51, mounting groove 52.

DESCRIPTION OF EMBODIMENTS

Embodiment: Visual Tooth Cleaning, Grinding and Polishing Instrument of the Invention Referring to FIG. 1 to FIG. 2-1, the visual tooth cleaning, grinding and polishing instrument of the invention includes a host 100, an oral observation instrument 200 and a cleaning and polishing tool 400. In the present embodiment, a flusher 409 is mounted on the oral observation instrument 200.

The host 100 includes a power system 11, a circuit system 12, a control system 13, a moving system 14 and a housing 15. The control system 13 is provided with a power switch 13-1 and a vibration drive switch 13-2. The power switch 13-1 and the vibration drive switch 13-2 are disposed on the housing 15.

In the present embodiment, the moving system 14 adopts an electromagnetic vibration drive mechanism, the moving system 14 includes a vibration generation device 14-1 and a vibration transmission device 14-2 capable of transmitting the vibration generated by the vibration generation device 14-1, a proximal end of the vibration transmission device 14-2 is connected to the vibration generation device 14-1, and a distal end of the vibration transmission device 14-2 is connected to the cleaning and polishing tool 400.

In the present embodiment, the vibration generation device 14-1 is an electromagnetic vibration device which may be an electromagnetic vibrator, or a magnetic suspension motor, or a piezoelectric transducer, or other forms of electromagnetic vibration devices. Herein, the applicant does not enumerate all forms, but the forms do not depart from the scope of protection of the present application.

Of course, the moving system 14 disposed in the host 100 may also be a motor-driven mechanical rotary moving system and the descriptions thereof are omitted herein.

Figure 21:
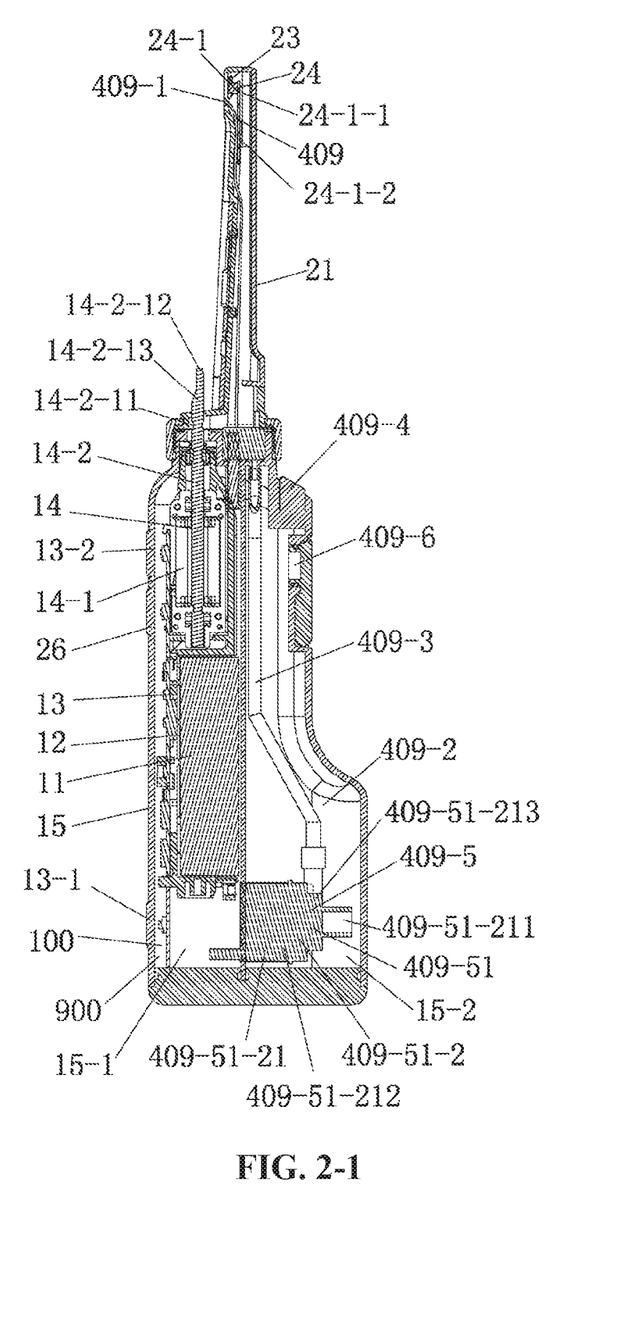
Figure 31:
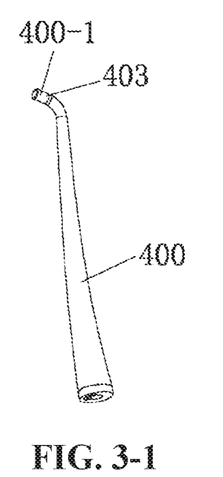

In the present embodiment, due to the flusher 409, an electrical mounting space 15-1 and a water and water path mounting space 15-2 are formed in the housing 15 of the host 100. Referring to FIG. 2-1, the power system 11, the circuit system 12 and the control system 13 are mounted in the electrical mounting space 15-1.

The power system 11, the control system 13 and the moving system 14 are connected together through the circuit system 12, and the power system 11 can drive the moving system to work, thereby driving the cleaning and polishing tool 400 to work.

The oral observation instrument 200 includes a housing 21, an illuminating system 23, an observation system 24 and a switch 26. The switch 26 is disposed on the housing 15 of the host 100. The illuminating system 23 and the puncture system 24 are disposed at the front end 200-1 of the oral observation instrument 200.

Figure 9:
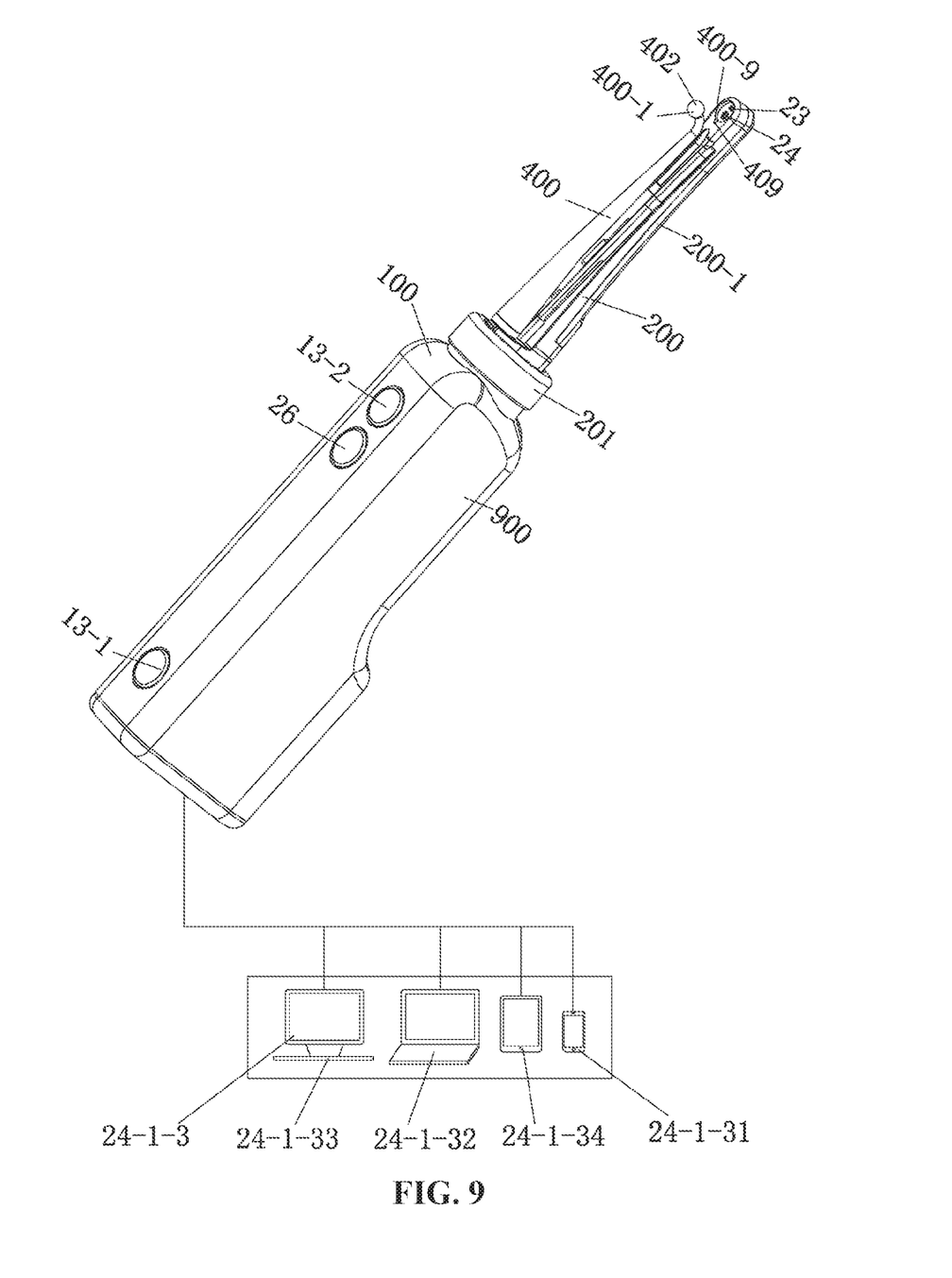
FIG. 9 is a working principle diagram of the visual tooth cleaning, grinding and polishing instrument of the invention connected to a display in a wireless mode.
Figure 10:
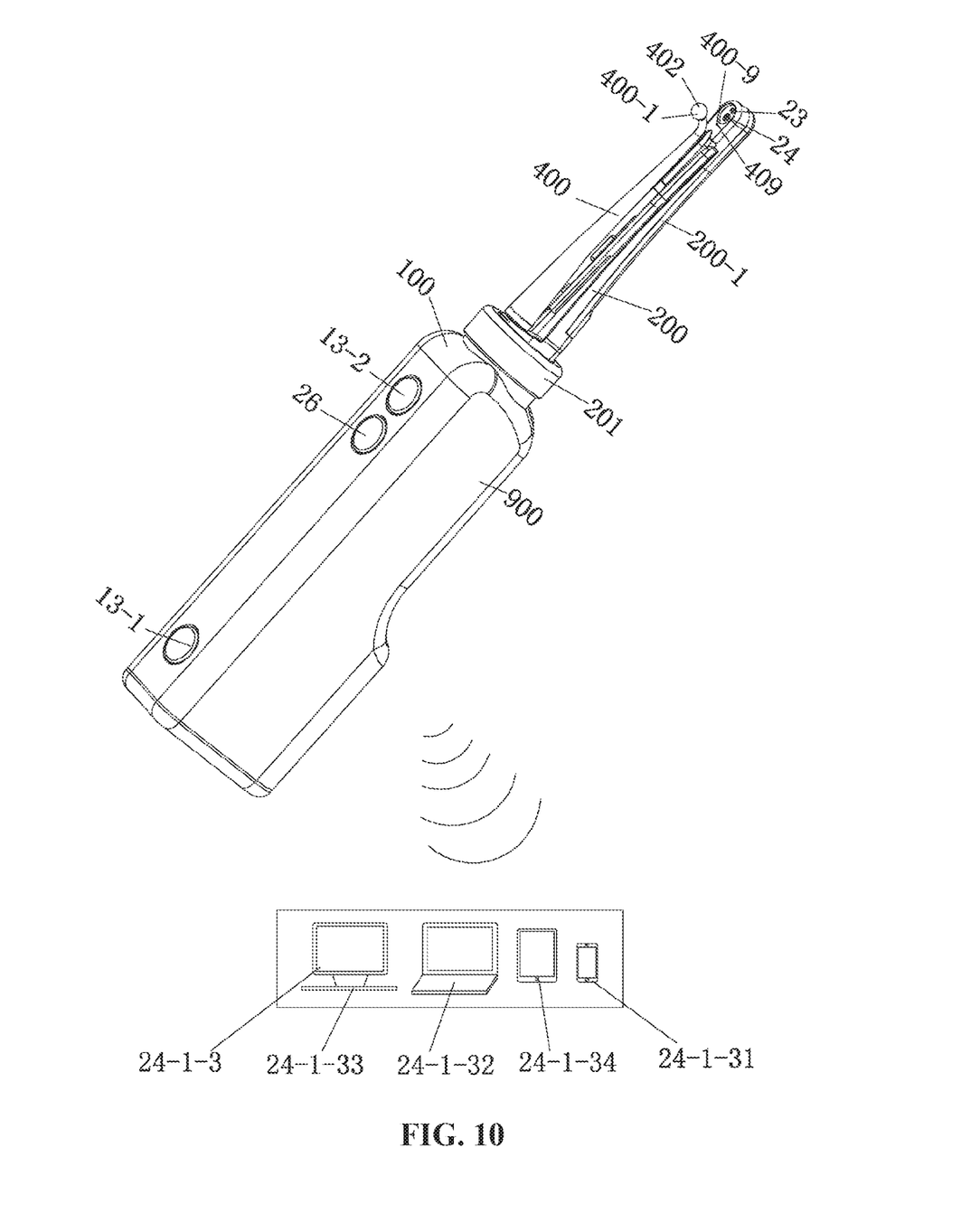
FIG. 10 is a working principle diagram of the visual tooth cleaning, grinding and polishing instrument of the invention connected to a display in a wired mode.
Figure 11:
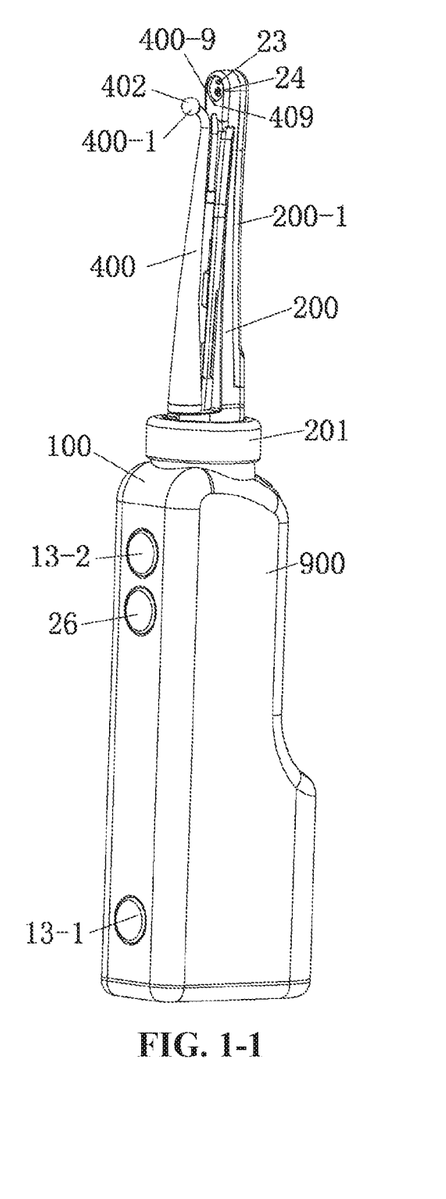

In the present embodiment, the observation system 24 is a camera system 24-1. The camera system 24-1 includes a camera 24-1-1, a data processing and output system 24-1-2 and a display 24-1-3. A picture shot by the camera 24-1-1 can be transmitted to the display 24-1-3 in time through the data processing and output system 24-1-2. Referring to FIG. 9 and FIG. 10, the display 24-1-3 may be a smart phone 24-1-31, or a computer 24-1-32, or a liquid crystal display/television 24-1-33, or a tablet computer 24-1-34.

In the present embodiment, the front end 200-1 of the oral observation instrument 200 is detachably connected to the host 100 through a detachable threaded connecting mechanism 201 in a mode of threaded connection.

The illuminating system 23, the observation system 24, the power system 11 and the switch 26 can also be connected together through the circuit system 12 and the control system 13, and the power system 11 can drive the illuminating system 23 and the observation system 24 of the oral observation instrument 200 to work, thereby controlling the work of the oral observation instrument 200.

Therefore, in the present application, the host 100 can not only drive the cleaning and polishing tool 400 but also supply a power source and a control system for the illuminating system 23, the observation system 24 and the like of the oral observation instrument 200, and can transmit the picture shot by the camera 24-1-1 of the observation system 24 to the display 24-1-3 such as the smart phone 24-1-31 of the observation system 24 in time, so as to achieve the purposes of cleaning the teeth while observing a process of cleaning the interdental space with the cleaning and polishing tool 400 and the cleaning effect instantly on a mobile phone, thereby effectively cleaning the teeth and the interdental space.

Figure 1:
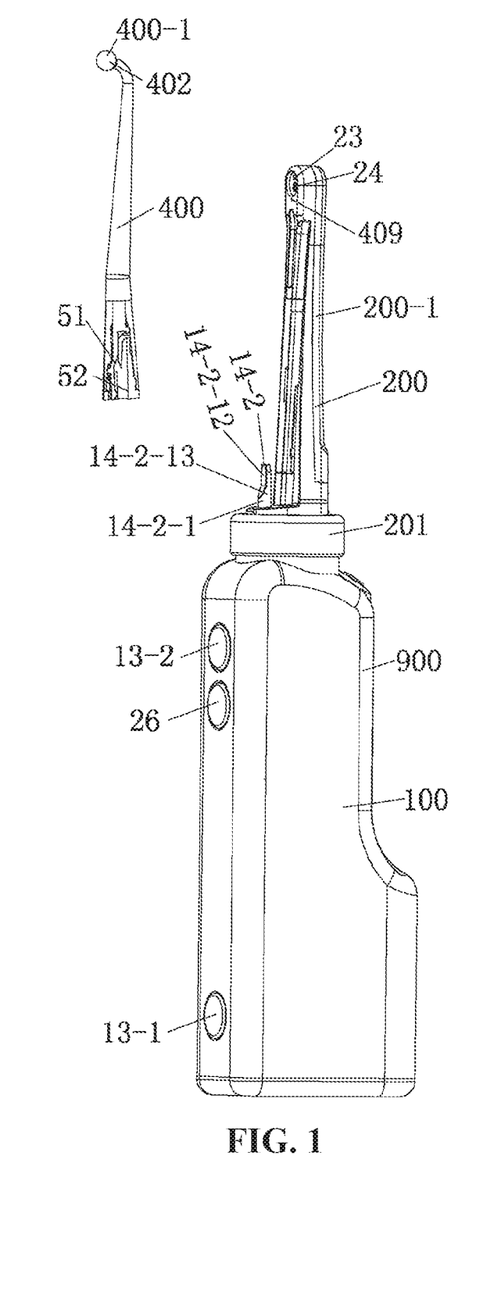
FIG. 1 is a schematic perspective view of a visual tooth cleaning, grinding and polishing instrument of the invention before a polishing and cleaning tool is mounted.
Figure 3:
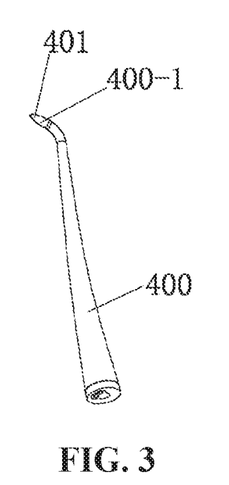
FIG. 3 is a schematic perspective view of a cleaning and polishing tool including a conical polishing head.

The cleaning and polishing tool 400 includes a polishing work part 400-1 with grinding and polishing functions. Referring to FIG. 1 and FIG. 1-1, in the present embodiment, the polishing work part 400-1 is geometrically shaped as a spherical cleaning and polishing head 402. Furthermore, referring to FIG. 3 and FIG. 3-1, the polishing work part 400-1 may also be a conical cleaning and polishing head 401 or a flat cleaning and polishing head 403. Herein, the applicant only enumerates the polishing heads of the above several shapes, and those skilled in the art may design polishing heads of various shapes according to actual conditions in combination with the prior art without departing from the scope of protection of the present application.

Figure 32:
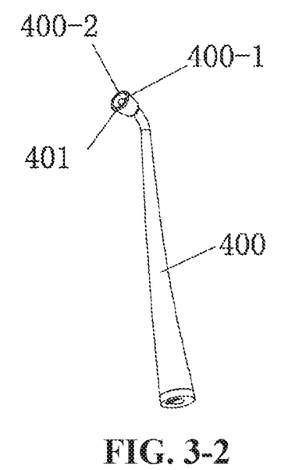

Referring to FIG. 3-2, the polishing work part 400-1 may also be provided with a flexible containing cavity 400-2 capable of containing polishing glue or toothpaste. A cleaning agent or a polishing agent such as polishing glue or polishing paste or toothpaste can be conveniently stored in the flexible containing cavity 400-2. In use, the polishing glue or polishing paste or toothpaste can be filled in the flexible containing cavity 400-2. When the polishing work part 400-1 works, the polishing glue or polishing paste or toothpaste in the flexible containing cavity 400-2 is compressed so as to further improve the cleaning effect of the polishing work part 400-1. Furthermore, because the polishing glue or polishing paste or toothpaste is compressed in the flexible containing cavity 400-2, it is possible to avoid unclear images of the observation system 24 caused by splashing of the polishing glue or polishing paste or toothpaste.

In the present embodiment, the cleaning and polishing tool 400 is detachably mounted at a distal end of the vibration transmission device 14-2. By virtue of a detachable mounting mode, the cleaning and polishing tool 400 can be conveniently removed from the host 100 for replacement, storage and carrying. In particular, by virtue of a detachable mounting mode, when other types of the interdental cleaning tools 400-9 need to be used for further cleaning, the cleaning and polishing tool 400 can be removed from the host and replaced with the interdental cleaning tool 400-9 to further clean the interdental space. Referring to FIG. 5 to FIG. 8-1, the interdental cleaning tool 400-9 can be selected from the interdental brush 407, or the dental floss 408, or the fetching forceps 410, or the hair brush 411 according to needs.

Figure 2:
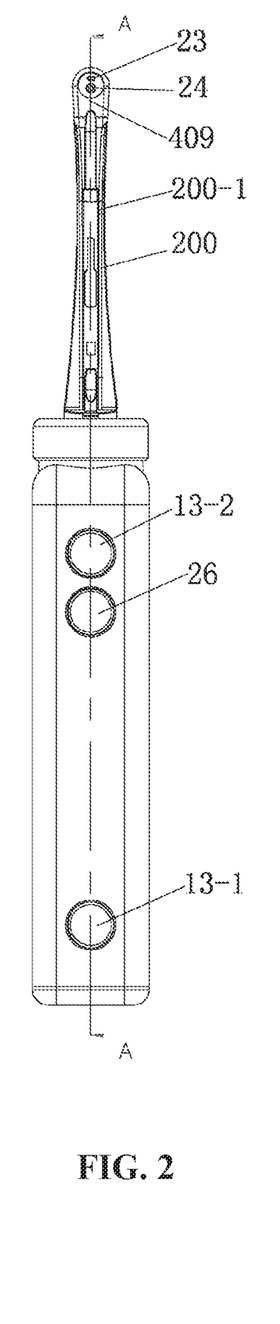
FIG. 2 is a front view of the visual tooth cleaning, grinding and polishing instrument of the invention with the cleaning and polishing tool removed.

In the present embodiment, the cleaning and polishing tool 400 is detachably mounted on the vibration transmission device 14-2 in a mode of concave-convex clamping connection. The vibration transmission device 14-2 includes a transmission shaft connecting part 14-2-1, and the transmission shaft connecting part 14-2-1 is provided with a connecting groove 14-2-1, a rotation stopping convex step 14-2-12 and a connecting shaft 14-2-13. The bottom of the cleaning and polishing tool 400 is provided with a connecting elastic sheet 51 and a mounting groove 52. A shape of the mounting groove 52 is matched with an outer contour of the transmission shaft connecting part 14-2-1. During connection, the mounting groove 52 of the cleaning and polishing tool 400 is aligned to the transmission shaft connecting part 14-2-1 and is slightly pressed down, the connecting elastic sheet 51 generates elastic deformation outward under the action of the connecting shaft 14-2-13, the transmission shaft connecting part 14-2-1 starts to enter the mounting groove 52 and continues to be pressed down until reaching the connecting groove 14-2-11, the external force of the connecting elastic sheet 51 is removed, and the connecting elastic sheet 51 returns to an original state and abuts in the connecting groove 14-2-11, thereby preventing the cleaning and polishing tool 400 from falling off from the vibration transmission device 14-2. Referring to FIG. 1 to FIG. 2-1, when the cleaning and polishing tool 400 needs to be removed, it is only necessary to forcibly pull out the cleaning and polishing tool 400 upward.

Of course, the cleaning and polishing tool 400 may also be detachably mounted on the vibration transmission device 14-2 in other modes, such as a mode of interference fit connection or a mode of rotational connection. Herein, the applicant does not enumerate the modes.

Figure 4:
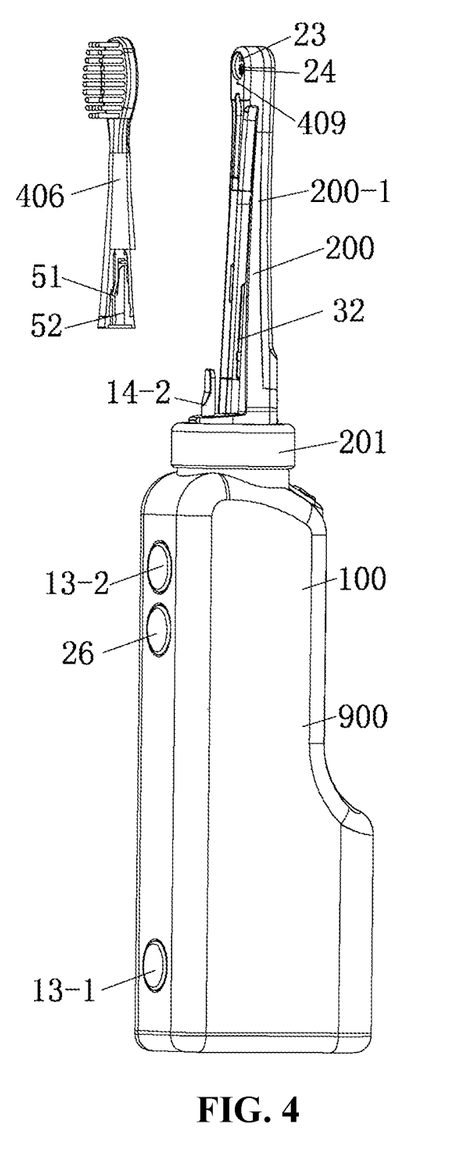
FIG. 4 is a schematic perspective view of the visual tooth cleaning, grinding and polishing instrument of the invention before an electric toothbrush head is mounted.
Figure 5:
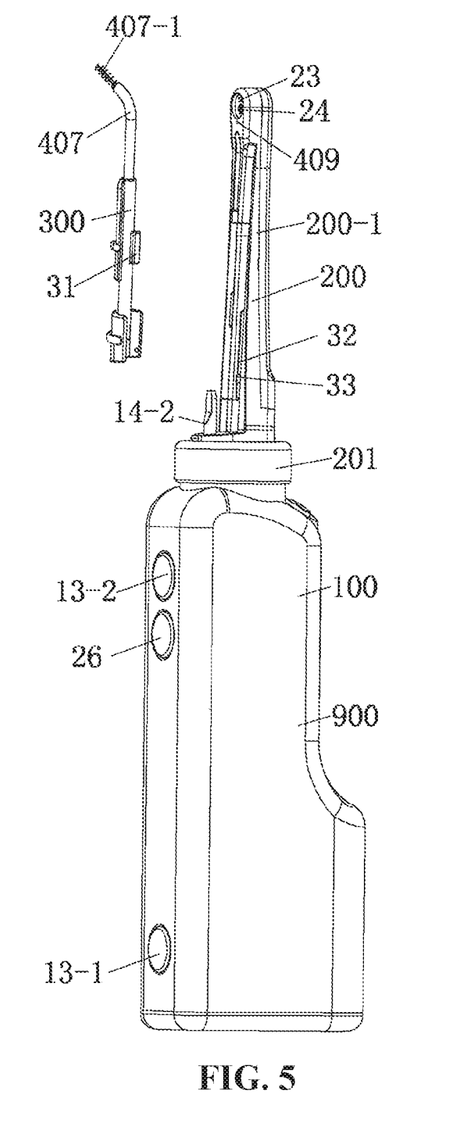
FIG. 5 is a schematic perspective view of the visual tooth cleaning, grinding and polishing instrument of the invention before an interdental brush is mounted.
Figure 6:
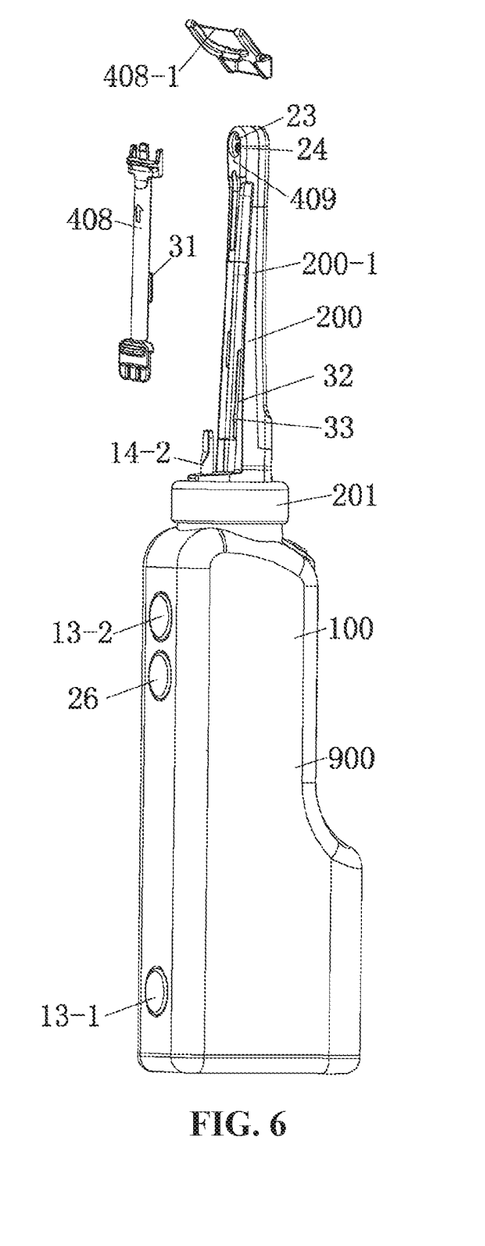
FIG. 6 is a schematic perspective view of the visual tooth cleaning, grinding and polishing instrument of the invention before a dental floss is mounted.
Figure 41:
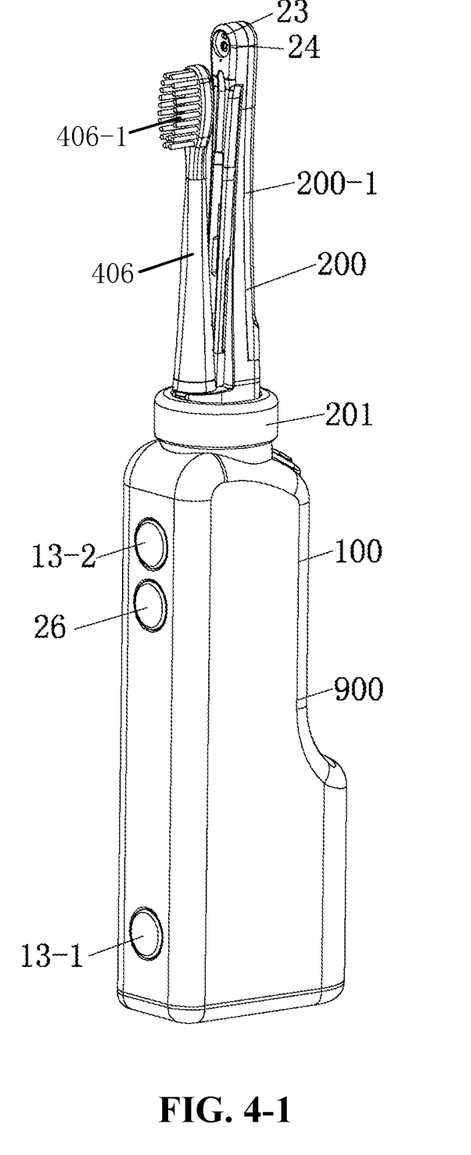
Figure 51:
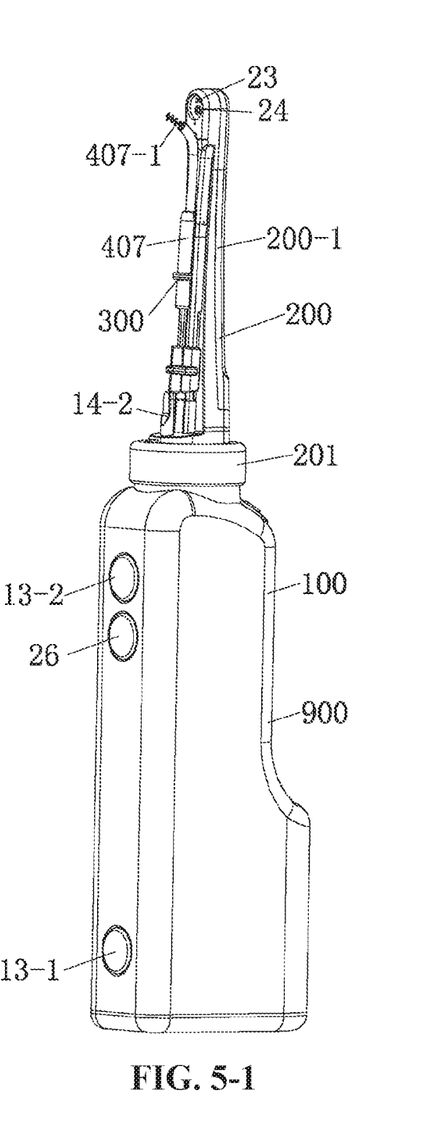
Figure 61:
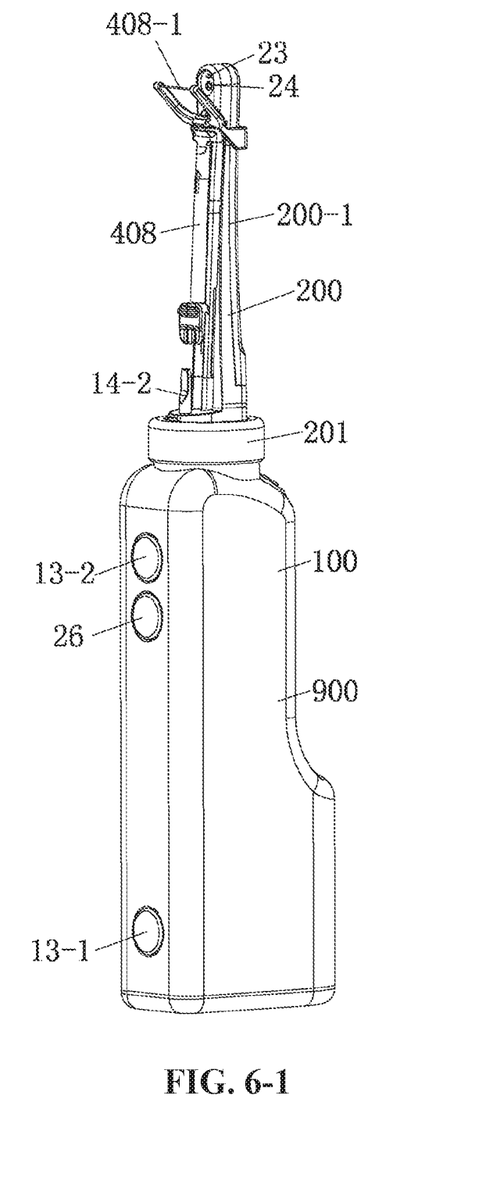
Figure 71:
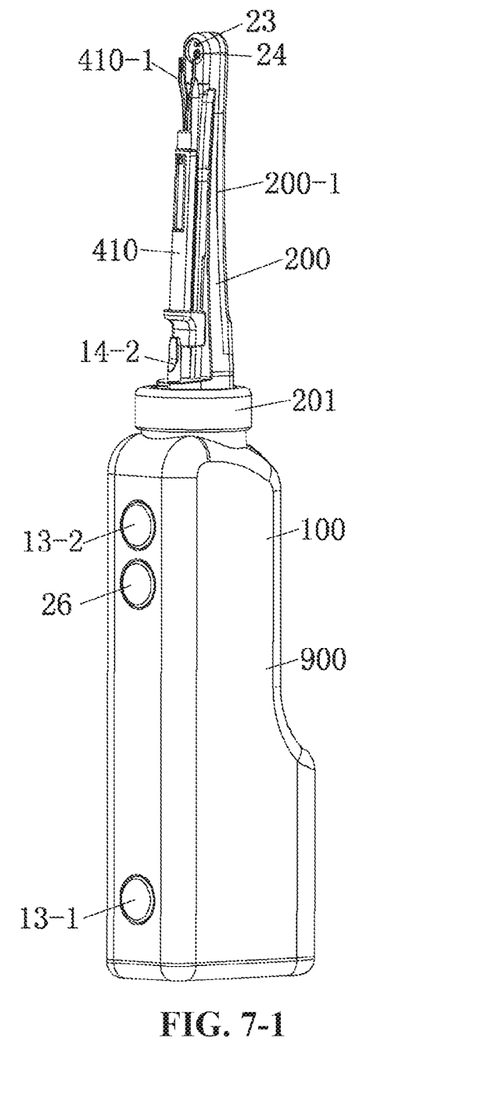
Figure 81:
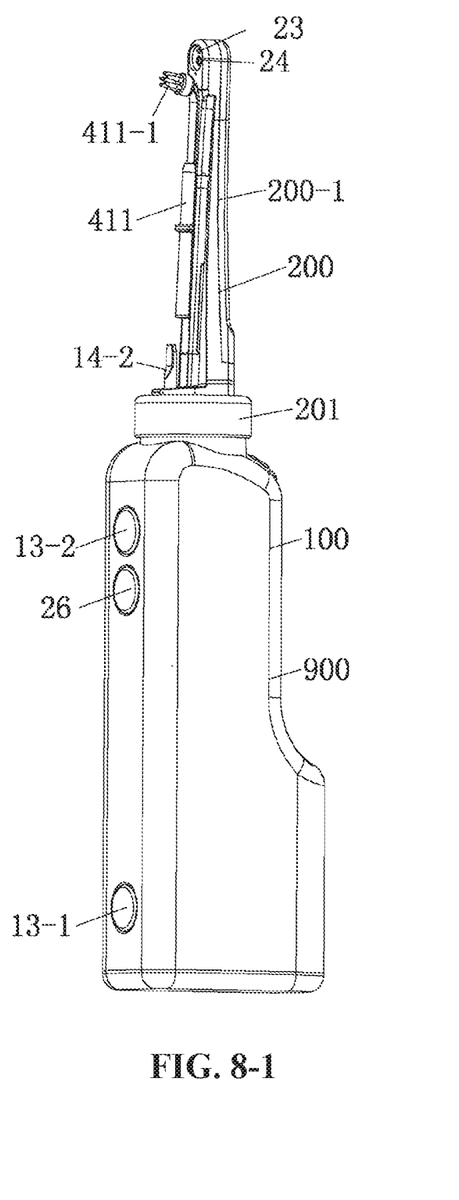

Referring to FIG. 4 and FIG. 4-1, an electric toothbrush head 406 may also be mounted on the host 100. When the electric toothbrush head 406 needs to be used for large-area brushing, the cleaning and polishing tool 400 is removed from the host 100, the electric toothbrush head 406 is mounted on the vibration transmission device 14-2 of the moving system 14, and the host 100 drives the electric toothbrush head 406 to work through the moving system 14. The work part of the electric toothbrush head 406 is within the field of view of the observation system 24 of the oral observation instrument 200.

When it is necessary to further clean the parts which are difficult to clean in the oral cavity specially, such as the interdental space, the cleaning and polishing tool 400 is removed from the vibration transmission device 14-2, and an appropriate interdental cleaning tool 400-9 is selected according to needs and is mounted on the oral observation instrument 200 for special cleaning. After use, the oral observation instrument 200, the cleaning and polishing tool 400 and the interdental cleaning tool 400-9 can be removed from the host so as to facilitate separate storage and cleaning.

Referring to FIG. 1 to FIG. 2-1, in the present embodiment, the flusher 409 is mounted on the oral observation instrument 200. The flusher 409 includes a sprayer 409-1, a water tank 409-2, a water pipe 409-3, a water spraying switch 409-4 and a pressurizing device 409-5. In the present embodiment, the sprayer 409-1 is built in the housing 21 of the front end 200-1 of the oral observation instrument 200. The water tank 409-2 and the pressurizing device 409-5 are mounted in the water and water path mounting space 15-2 of the housing 15 of the host 100. The sprayer 409-1 is mounted near the observation system 24 of the front end 200-1 of the oral observation instrument 200 to ensure that the water sprayed by the sprayer 409-1 can be maintained within the field of view of the observation system 24, so that the cleaning effect of the flusher 409 on the oral cavity is conveniently observed.

In the present embodiment, the pressurizing device 409-5 is an electric pressurizing device 409-51. The electric pressurizing device 409-51 is an electric water pressurizing device 409-51-2. The electric water pressurizing device 409-51-2 is a submersible pump 409-51-21.

The submersible pump 409-51-21 includes a water inlet system 409-51-211, a pressurizing system 409-51-212 and a drainage system 409-51-213.

The submersible pump 409-51-21 is mounted at the bottom of the water tank 409-2. The drainage system 409-51-211 is connected to the water pipe 409-3. Referring to FIG. 2-1, after the power system 11 supplies power for the submersible pump 409-51-21, the pressurizing system 409-51-212 works to pressurize the water entering, through the water inlet system 409-51-211, the submersible pump 409-51-21, the water spraying switch 409-4 is turned on, and then the drainage system 409-51-213 can spray the pressurized water from the sprayer 409-1 through the water pipe 409-3 so as to flush the teeth.

The water tank 409-2 is also provided with a water filling hole 409-6, and water can be replenished into the water tank 404-2 through the water filling hole 409-6.

In the present embodiment, because the sprayer 409-1 of the flusher 409 is built in the housing 21 of the front end 200-1 of the oral observation instrument 200, the front end of the oral observation instrument 200 may also be combined and matched with other interdental cleaning tools 400-9, such as the interdental brush 407, the dental floss 408, the fetching forceps 410, the hair brush 411 or other cleaning and polishing tools. During cleaning, the oral cavity is flushed with water while being cleaned with the interdental brush 407, the dental floss 408, the fetching forceps 410, the hair brush or other cleaning and polishing tools according to needs. In particular, an operation process can be transmitted to various displays in real time. Under direct vision, food residues are accurately cleared or various foreign matters in the oral cavity are taken out, thereby greatly improving the cleaning effect. Furthermore, the use is safer and more convenient.

In particular, under the direct vision of the oral observation instrument 200, the cleaning is performed with water by using the flusher 409 while the grinding, polishing and cleaning are performed by using the cleaning and polishing tool 400, so that the cleaning efficiency can be improved.

The interdental cleaning tool 400-9 is detachably mounted at the front end 200-1 of the oral observation instrument 200 through the connecting mechanism 300.

The connecting mechanism 300 may be an independent component which can be disposed on the interdental cleaning tool 400-9 or disposed on the oral observation instrument 200. Or a portion of the detachable mechanical connecting mechanism is disposed on the interdental cleaning tool 400-9, and another portion of the detachable mechanical connecting mechanism is disposed on the oral observation instrument 200 to form a combined type mechanical connecting mechanism.

In the present embodiment, the connecting mechanism 300 is in concave-convex clamping connection, or the connecting mechanism 300 may also be in slide groove connection, or pin connection, or key connection, or threaded connection, or screw connection, or buckle connection, or hook connection, or interference fit connection. Those skilled in the art can make various specific product designs according to the technical solutions disclosed by the invention without departing from the scope of protection of the invention.

In the present embodiment, the housing 21 of the oral observation instrument 200 is provided with a positioning groove 32 and a clamping block 33 capable of being connected to the interdental cleaning tool 400-9. The inverted T-shaped positioning block 31 on the interdental cleaning tool 400-9 can be embedded in the positioning groove 32, and the clamping block 33 can prevent the interdental brush 407 from sliding backward. The positioning block 31, the positioning groove 32 and the clamping block 33 cooperate to form the connecting mechanism 300.

Referring to FIG. 5 to FIG. 8-1, a brush head 407-1 of the interdental brush 407, a line 408-1 of the dental floss 408, a water column sprayed by the flusher 409, a forceps head 410-1 of the fetching forceps 410 and a head 411-1 of the hair brush 411 are within the field of view of the observation system 24 of the oral observation instrument 200.

In the present embodiment, a direction of the water column sprayed by the flusher 409 is substantially the same as a direction in which the interdental brush 407 or the dental floss 408 enters the interdental space. Thus, when the brush head 407-1 of the interdental brush 407 or the line 408-1 of the dental floss 408 moves back and forth between the interdental spaces for cleaning, the water sprayed by the sprayer 407-1 can play an auxiliary role in flushing the food residues at the interdental spaces.

Figure 7:
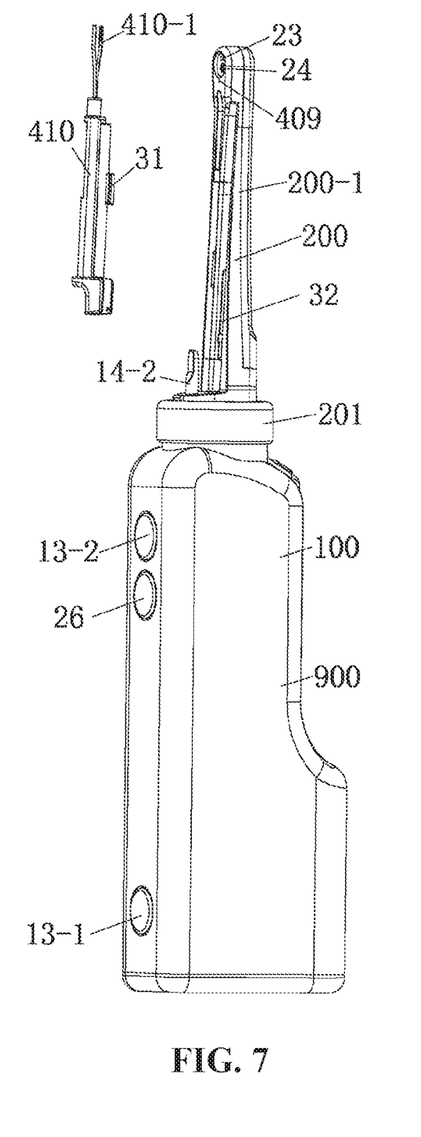
FIG. 7 is a schematic perspective view of the visual tooth cleaning, grinding and polishing instrument of the invention before a pair of fetching forceps is mounted.
Figure 8:
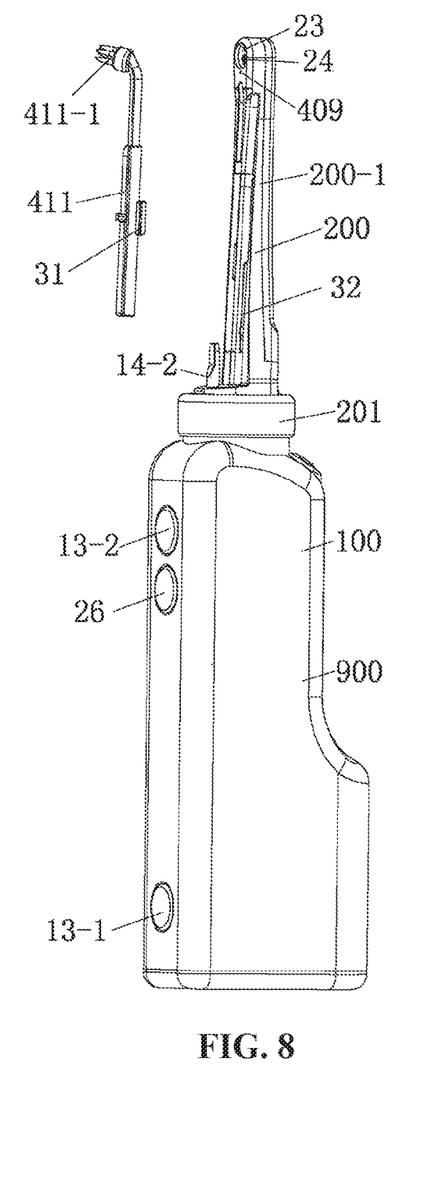
FIG. 8 is a schematic perspective view of the visual tooth cleaning, grinding and polishing instrument of the invention before a hair brush is mounted.

Furthermore, referring to FIG. 7 to FIG. 8-1, a process of connecting the oral observation instrument 200 to other interdental cleaning tools 400-9, such as the fetching forceps 410 and the hair brush 411, through the connecting mechanism 300 will not be described herein, and it is only necessary to ensure that the forceps head 410-1 of the fetching forceps 410 and the head 411-1 of the hair brush 411 are placed within the field of view of the observation system 24 for direct observation in a cleaning process.

During use, firstly, the cleaning and polishing tool 400 is mounted on the moving system 14 of the host 100, the oral observation instrument 200 is mounted in place, the power switch 13-1 is pressed, then, the switch 26 is turned on, the oral observation instrument 200 is started, and then, the vibration drive switch 13-2 is pressed, to clean the dental calculus or dental plaque or pigmentation by the cleaning and polishing tool 400. In this case, under the action of the oral observation instrument 200, an oral cleaning process is displayed on the display 24-1-3 in real time, so that the cleaning process and the cleaning effect can be observed in real time.

If there are parts needing to be further cleaned specially, the interdental cleaning tool 400-9, such as the interdental brush 407, the dental floss 408, the fetching forceps 410, the hair brush 411 or the like, can be mounted at the front end 200-1 of the oral observation instrument 200 through the connecting mechanism 300 as needed, and under the observation of the observation system 24 of the oral observation instrument 200, the parts needing to be further cleaned specially, such as the interdental space, can be further cleaned by using the interdental cleaning tool 400-9.

The visual tooth cleaning, grinding and polishing instrument of the invention can achieve the purposes of cleaning the teeth while observing a process of cleaning the dental calculus, dental plaque and pigmentation on the surface of the teeth with the cleaning and polishing tool 400 and the cleaning effect instantly on a mobile phone, thereby effectively cleaning, grinding and polishing the teeth. Furthermore, the visual tooth cleaning, grinding and polishing instrument can be used in conjunction with a special interdental cleaning tool 400-9 so as to accurately clean the parts which are difficult to clean, such as the interdental space.

In the present embodiment, the electric pressurizing device 404-51 is a submersible pump 404-51-21. Furthermore, the electric pressurizing device 404-51 may also be an electric air pressurizing device or other types of electric water pressurizing devices, such as a water pump.

When the oral observation instrument 200 of the visual tooth cleaning, grinding and polishing instrument of the invention is used for visual cleaning in time, if the right and left hands are exchanged for operation, the picture on the display 24-1-3 may be inverted. In this case, it is only necessary to activate a picture adjusting button in the display 24-1-3, such as click a suspension button on the display, to invert the picture and maintain a normal relationship between upper and lower teeth for convenient operation.

Furthermore, if the visual tooth cleaning, grinding and polishing instrument of the invention is used for cleaning flexible tissues in the oral cavity, such as coated tongue and gingivae, the polishing work part 400-1 is made of a flexible material to play roles in vibrating, massaging and cleaning.

If the visual tooth cleaning, grinding and polishing instrument of the invention is used for cleaning the dental calculus, dental plaque and the like, the polishing work part 400-1 may be made of a rigid material, such as a diamond bur, an inverted cone and a grinding head, and the polishing work part 400-1 is designed into different shapes as needed and made of a corresponding material.

It should be noted that the structures disclosed and described herein may be replaced with other structures having the same effect, and the embodiments described herein are not the only structures that can implement the invention. Although the preferred embodiments of the invention have been described herein, it is apparent to those skilled in the art that the embodiments are merely examples, and various variations, modifications, and replacements may be made by those skilled in the art without departing from the invention. Therefore, the protection scope of the invention should be subject to the spirit and scope of the appended claims of the invention.

The invention claimed is:

1. A system for visual tooth cleaning, grinding and polishing, the system comprising:
    a host having a first housing and comprising a power system, a circuit system, a control system, and a moving system, wherein:
        the power system, the control system, and the moving system are operably connected together through the circuit system;
        the power system, the circuit system, the moving system, and the control system are positioned within the first housing; and
        the moving system includes a connecting shaft that protrudes from a first end of the first housing;
    an oral observation instrument connected to the host at the first end of the first housing, the oral observation instrument comprising a second housing, an illuminating system, an observation system, and a positioning groove on the second housing, wherein:
        the illuminating system and the observation system are positioned in the second housing; and
        the illuminating system, the observation system, and the power system are operably connected together through the circuit system and the control system;
    a cleaning and polishing tool adapted to detachably mount to the moving system of the host via the connecting shaft, wherein while mounted to the moving system, the cleaning and polishing tool is drivable by the moving system in accordance with the control system, and wherein a work part of the cleaning and polishing tool is within a field of view of the observation system while mounted to the moving system; and
    an interdental cleaning tool, distinct from the cleaning and polishing tool, the interdental cleaning tool adapted to detachably mount to only the oral observation instrument via the positioning groove, wherein the interdental cleaning tool is mountable in place of the cleaning and polishing tool, and wherein a work part of the interdental cleaning tool is within the field of view of the observation system while mounted to the oral observation instrument.

2. The system according to claim 1, wherein the moving system is a vibration system capable of generating vibration.

3. The system according to claim 2, wherein the vibration system comprises:
    a vibration generation device; and
    a vibration transmission device capable of transmitting the vibration generated by the vibration generation device, wherein one end of the vibration transmission device is connected to the vibration generation device, and wherein the connecting shaft at the other end of the vibration transmission device is connected to the cleaning and polishing tool while the cleaning and polishing tool is mounted on the vibration system.

4. The system according to claim 3, wherein the vibration generation device is an electromagnetic vibration device comprising one of: an electromagnetic vibrator, a magnetic suspension motor, or a piezoelectric transducer.

5. The system according to claim 3, wherein the cleaning and polishing tool is detachably mounted on the connecting shaft via one of: a concave-convex clamping connection, an interference fit connection, or a rotational connection.

6. The system according to claim 1, wherein the cleaning and polishing tool comprises a polishing work part having grinding and polishing functions and geometrically shaped as one of: a conical cleaning and polishing head, a spherical cleaning and polishing head, or a flat cleaning and polishing head.

7. The system according to claim 6, wherein the polishing work part is provided with a flexible containing cavity capable of containing polishing glue or toothpaste.

8. The system according to claim 1, wherein the cleaning and polishing tool comprises an electric toothbrush head.

9. The system according to claim 1, wherein the interdental cleaning tool comprises one of: an interdental brush, dental floss, or a pair of fetching forceps.

10. The system according to claim 1, further comprising a flusher comprises a sprayer, a water tank, a water pipe, a water spraying switch and a pressurizing device;
    wherein the water tank and the pressurizing device are disposed within the first housing of the host; and
    wherein the sprayer is mounted near the observation system at a front end of the oral observation instrument such that water sprayed by the sprayer is within a field of view of the observation system.

11. The system according to claim 10, wherein the sprayer of the flusher is built in the second housing of the front end of the oral observation instrument.

12. The system according to claim 10, wherein the flusher is configured to be used in conjunction with the interdental cleaning tool or the cleaning and polishing tool.

13. The system according to claim 12, wherein the interdental cleaning tool comprises an interdental brush, and wherein the flusher is oriented such that a water column sprayed by the flusher is in substantially the same direction as the direction in which the interdental brush enters an interdental space.

14. The system according to claim 1, wherein the cleaning and polishing tool comprises a connecting elastic sheet adapted to prevent the cleaning and polishing tool from falling off the moving system.

15. The system according to claim 1, wherein the observation system comprises a camera communicatively coupled to a display.

16. The system according to claim 1, wherein the oral observation instrument further comprises a clamping block, and wherein the interdental cleaning tool mounts to the oral observation instrument via the positioning groove and the clamping block.

17. The system according to claim 16, wherein the interdental cleaning tool includes a positioning block adapted to connect with the positioning groove and the clamping block to mount the interdental cleaning tool to the oral observation instrument.

* * * * *